United States Patent [19]

Epstein et al.

[11] 4,420,437

[45] Dec. 13, 1983

[54] PREPARATION OF A 2-ARALKYL-5,5-DIALKYL-1,3,2-DIOXAPHOSPHORINAN-2-ONE FROM 2-ARALKOXY-5,5-DIALKYL-1,3,2-DIOXAPHOSPHORINANE

[75] Inventors: Peter F. Epstein, Glen Burnie, Md.; Richard D. Peveler, Wyckoff; Michael H. Fisch, Wayne, both of N.J.

[73] Assignee: Witco Chemical Corporation, New York, N.Y.

[21] Appl. No.: 290,532

[22] Filed: Aug. 6, 1981

[51] Int. Cl.³ .............................................. C07F 9/40
[52] U.S. Cl. ..................................... 260/969; 260/937
[58] Field of Search ........................................ 260/969

[56] References Cited

U.S. PATENT DOCUMENTS 3,483,279 12/1969 Davis et al. ................... 260/969
3,801,677 4/1974 Baranauckas et al. ......... 260/969
4,288,063 10/1980 Granzow ...................... 260/45.7 P
4,311,652 1/1982 Abramson et al. ............ 260/969

OTHER PUBLICATIONS

Kosolapoff, "Organophosphorus Compounds", (1950), pp. 121–122.

Primary Examiner—Anton H. Sutto
Attorney, Agent, or Firm—Wallenstein, Wagner, Hattis, Strampel & Aubel

[57] ABSTRACT

A process for preparing a 2-aralkyl-5,5-dialkyl-1,3,2-dioxaphosphorinan-2-one by heating a 2-aralkyloxy-5,5-dialkyl-1,3,2-dioxaphosphorinane such as the novel 2-benzyloxy-5,5-dimethyl-1,3,2-dioxaphosphorinane, with a catalytic quantity of an aralkyl halide. The aralkyl halide can be recovered and recycled.

5 Claims, No Drawings

PREPARATION OF A 2-ARALKYL-5,5-DIALKYL-1,3,2-DIOXAPHOSPHORINAN-2-ONE FROM 2-ARALKOXY-5,5-DIALKYL-1,3,2-DIOXAPHOSPHORINANE

BACKGROUND OF THE INVENTION

This invention relates to a new and practical process for preparing a 2-aralkyl-5,5-dialkyl-1,3,2-dioxaphosphorinan-2-one represented by the formula:

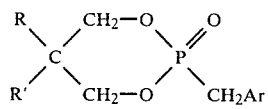

in which R is an alkyl group having 1 to 2 carbon atoms and R' is an alkyl group having 1 to about 9 carbon atoms, and Ar is an aryl group having 6 to about 18 carbon atoms.

Compounds represented by formula (I) are useful flame retardants for certain plastics, as disclosed, for example, by A. Granzow in U.S. Pat. No. 4,288,063 of Oct. 14, 1980, incorporated herein by reference. A particularly useful property of these compounds is that they are efficient in imparting flame retardance at modest use levels while having a minimal adverse effect on the useful properties of the plastic, such as an undesired softening or plasticizing effect. Moreover, these compounds do not require the joint use of halogenated additives such as chlorinated paraffin or brominated phosphate esters, which aside from their cost, can have their own adverse effect on the properties of the plastic.

K. D. Bartle and coworkers in 1967 disclosed a preparation of the compound having formula I in which R and R' are methyl and Ar is phenyl (Tetrahedron, vol. 23, p. 1702) by heating 5,5-dimethyl-2-methoxy-1,3,2-dioxaphosphorinane (prepared by transesterification between trimethyl phosphite and 2,2-dimethylpropane-1,3-diol) with benzyl chloride for 12 hours at 170°–180° C. The yield is stated to be 60% of theoretical. As a practical method of preparation, however, the synthesis of Bartle is unsatisfactory, because the first intermediate, trimethyl phosphite, is difficult to prepare and highly volatile and odorous, and the yield in the transesterification with 2,2-dimethylpropane-1,3-diol is only 50%, making the overall yield (from trimethyl phosphite) only 30%.

Bartle's synthesis can be represented by the reaction equation:

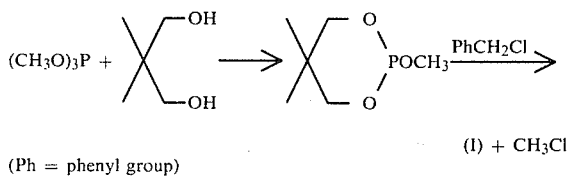

(I) + CH$_3$Cl (Ph = phenyl group)

It can be seen that the second step of this sequence is an instance of the Arbuzov reaction in which the methyl group of the 5,5-dimethyl-2-methoxy-1,3,2-dioxaphosphorinane is displaced as methyl chloride. The art, however, has recognized that dioxaphosphorinanes with larger alkoxy substituents do not undergo displacement in the same way; instead, phosphonates are formed in which the dioxaphosphorinane ring is opened and no alkyl halide is produced. As a source of this statement, Bartle and coworkers cite Wadsworth and Emmons (J. Amer. Chem. Soc. 1962, vol. 84, page 610) and the latter authors in turn cite a 1958 paper by A. E. Arbuzov, the discoverer of the reaction named for him, in which displacement of an organic halide on a phosphite ester links the organic group of the halide to phosphorus through carbon while an organic group of the phosphite ester is displaced as halide.

Consequently, one is led to conclude that a 2-alkoxy-1,3,2-dioxaphosphorinane reactant with a benzyl halide for making a 2-benzyl 1,3,2-dioxaphosphorinan-2-one must be a 2-methoxy-1,3,2-dioxaphosphorinane, since 1,3,2-dioxaphosphorinanes with larger 2-alkoxy substituents would give a different and undesirable type of product.

A. Granzow in U.S. Pat. No. 4,288,063 of Oct. 14, 1980 also disclosed the preparation of compounds which can be represented by formula (I) in which R and R' are methyl and Ar is phenyl and 2,4,6-trimethylphenyl, by heating the aralkyl chloride with neopentyl phosphite and a strong base (sodium hydride) in dimethylformamide (DMF) solvent. The course of these preparations can be illustrated by the following reaction equations:

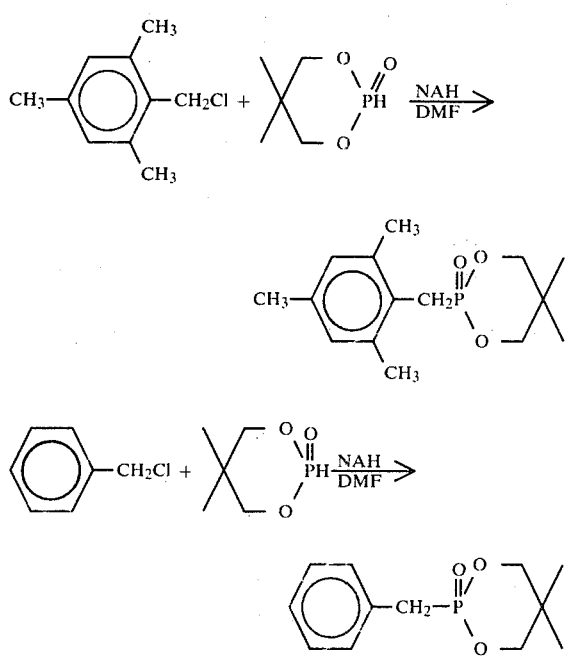

Granzow describes a 65% yield for the reaction with 2,4,6-trimethylbenzyl chloride and does not indicate the yield for the reaction with benzyl chloride. In any event, the need to use expensive sodium hydride and dimethylformamide and to handle and dispose of by-product hydrogen gas with its attendant safety hazards make Granzow's method impractical for industrial use.

SUMMARY OF THE INVENTION

In accordance with this invention, a 2-aralkyl-5,5-dialkyl-1,3,2-dioxaphosphorinan-2-one is prepared having the formula:

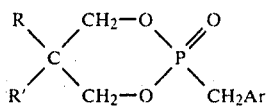

(I)

in which R is an alkyl group having 1 to 2 carbon atoms and R' is an alkyl group having 1 to about 9 carbon atoms, and Ar is an aryl group having 6 to about 18 carbon atoms, by heating a 2-aralkyloxy-5,5-dialkyl-1,3,2-dioxaphosphorinane (II) with a catalytic quantity of an aralkyl halide in which the halogen is chlorine, bromine or iodine, and recovering a 2-aralkyl-5,5-dialkyl-1,3,2-dioxaphosphorinan-2-one from the mixture.

The present process is highly efficient in providing an excellent yield of the desired product (I) and in avoiding wastage of materials. Modest quantities of the aralkyl halide catalyst only are required, as little as 0.1% by weight of the combined reactants being effective. The aralkyl halide catalyst is not consumed in the reaction in which the desired product is formed, and can be recovered for reuse. Accordingly, extreme economy in catalyst usage is not required, particularly when a large excess of catalyst, even as high as about 70% by weight of the combined reactants maybe used, because the excess is not deleterious to the reaction.

The intermediate 2-aralkyloxy-5,5-dialkyl-1,3,2-dioxaphosphorinane (II) used in the present process is a novel compound which is prepared from commercially available starting materials by a two-stage procedure illustrated by the following reaction equations:

First Stage

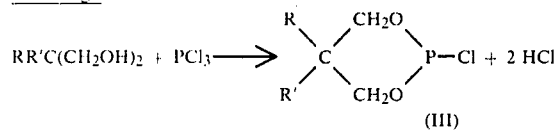

Second Stage

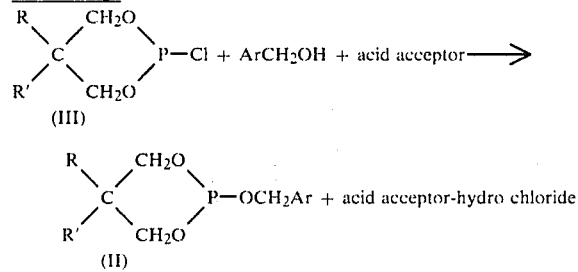

In the first stage, a 2,2-dialkylpropane-1,3-diol and phosphorusn trichloride react to give a 2-chloro-1,3,2-dioxaphosphorinane. In the second stage, (III) reacts with an aralkyl alcohol in the presence of an acid acceptor to give the intermediate 2-aralkyloxy-1,3,2-dioxaphosphorinane (II), after separation from the neutralized form of the acid acceptor by washing or filtration. Excellent yields are obtained in both stages. Frequently, the entire reaction product from the first stage is used without further purification in proceeding immediately to the second stage.

DESCRIPTION OF PREFERRED EMBODIMENTS

In the 2-aralkyl-5,5-dialkyl-1,3,2-dioxaphosphorinan-2-one prepared by the process of this invention, R in Formula I can be methyl or ethyl; R' can be for example, methyl, ethyl, propyl, isopropyl, n-butyl, isobutyl, sec-butyl, tert-butyl, n-pentyl, isoamyl, 2,2-dimethylpropyl, 2-ethylbutyl, n-hexyl, n-heptyl, 3,5-dimethylhexyl, n-octyl, 2-ethylhexyl, 3,5,5-trimethylhexyl, cyclohexyl, or n-nonyl; Ar can be phenyl, tolyl, xylyl, p-t-butylphenyl, cumyl, 2-methyl-5-isopropylphenyl, 2,3,5-trimethylphenyl, tert-octylphenyl, nonylphenyl, dodecylphenyl, 1-naphthyl, 2,6-dimethylnaphthyl, 9-anthracenyl, 9-phenanthryl, and the like.

The aralkyl halide catalyst used in the process of this invention to prepare the desired 2-aralkyl-5,5-dialkyl-1,3,2-dioxaphosphorinan-2-one can be an aralkyl chloride, bromide, or iodide. Suitable aralkyl halides are, for example, benzyl chloride, benzyl iodide, benzyl bromide, p-t-butylbenzyl iodide, 3,4-dimethylbenzyl bromide, p-ethylbenzyl iodide, 1-chloromethylanphthalene, and the like. The iodides, particularly benzyl iodide, is preferred because it is effective in small quantities and at low temperatures.

Suitable 2-aralkyloxy-5,5-dialkyl-1,3,2-dioxaphosphorinane intermediates are, for example, 2-benzyloxy-5,5-dimethyl-1,3,2-dioxaphosphorinane, 2(p-ethylbenzyloxy)-5,5-dimethyl-1,3,2-dioxaphosphorinane, 2(3',4'-dimethylbenzyloxy)-5,5-diethyl-1,3,2-dioxaphosphorinane; the 2-benzyloxy-5,5-dimethyl-1,3,2-dioxaphosphorinane being particularly preferred.

In the aralkyl alcohol used together with a 2-chloro-5,5-dialkyl-1,3,2-dioxaphosphorinane to prepare the 2-aralkyloxy-5,5-dialkyl-1,3,2-dioxaphosphorinane intermediate used in the present process aralkyl moiety is the same as in the desired product. Accordingly, suitable aralkyl alcohols include benzyl alcohol, p-t-butylbenzyl alcohol, 3,4-dimethylbenzyl alcohol, p-ethylbenzyl alcohol, and naphthalene-1-methanol. To prepare the 2-chloro-5,5-dialkyl-1,3,2-dioxaphosphorinane intermediate, any 2,2-dialkylpropane-1,3-diol having the R and R' groups in the desired product can be used. Suitable diols include 2,2-dimethylpropane-1,3-diol, 2-ethyl-2-methylpropane-1,3-diol, 2,2-diethylpropane-1,3-diol, and 2-methyl-2-butylpropane-1,3-diol. 2,2-Dimethylpropane-1,3-diol is preferred.

The process of this invention is usually carried out in the liquid phase at a temperature at which the desired reaction proceeds at a convenient rate, preferably between about 120° C. and 280° C., with the temperature usually in the lower range when an aralkyl iodide is used as catalyst. The process can be operated at atmospheric, subatmospheric or superatmospheric pressure, as desired. Any exotherm accompanying the reaction can be moderated by external cooling to keep the temperature in the desired range, or by the use of an inert solvent whose vaporization can take up the heat of reaction, or by the use of a portion of the reaction product as a heat sink, such as in a semi-continuous or continuous operation of the process. Any inert solvent that does not affect the reactants or product of the process can be used, particularly hydrocarbons such as heptane, toluene or xylene; ethers such as 1,4-dioxane or n-butyl ether; and esters such as butyl acetate or benzyl benzoate. Solvents that contain water, alcohols, amines, or halides, are best avoided since these can affect either of the reactants or the reaction product.

The desired 2-aralkyl-5,5-dialkyl-1,3,2-dioxaphosphorinan-2-one prepared by the process of this invention can be recovered from the reaction mixture by conventional techniques such as solvent stripping, distillation, or crystallization. When the solution of aralkyl halide catalyst is kept low relative to the product prepared, i.e., wherein the product is present in amounts greater than about 65–70% by weight, the latter separates as a crystalline phase on cooling the reaction mixture and can be collected by filtering or centrifuging; the mother liquors containing solvent, aralkyl halide, and a small amount of product can be recycled to a subsequent preparation.

In the preparation of the intermediate 2-aralkyloxy-5,5-dialkyl-1,3,2-dioxaphosphorinane of this invention, the first stage reaction of phosphorous trichloride with a 2,2-dialkylpropane-1,3-diol and the second stage reaction of 2-chloro-5,5-dialkyl-1,3,2-dioxaphosphorinane, resulting from the first stage, with aralkyl alcohol and acid acceptor, are conveniently carried out in the liquid phase at a temperature in the range of 20° C. to 160° C. An inorganic or organic acid acceptor can be used. Suitable acid acceptors include lime, magnesium oxide, anhydrous ammonia, potash, caustic soda, lithium bicarbonate, and organic tertiary amines such as trimethylamine, N,N-diethylaniline, N,N-dimethyl-N-2-ethylhexylamine and the like as known in the art. As the second stage reaction proceeds, the acid acceptor is progressively converted to its hydrochloride adduct or salt. Suitably a modest excess of acid acceptor, typically 10 mole percent, is used.

The 2-aralkoxy-5,5-dialkyl-1,3,2-dioxaphosphorinane product of the second stage reaction is recovered by removing the hydrochloride adduct or salt arising from the use of the acid acceptor, and then stripping off the solvent. The remaining product can be used without further purification or distilled under reduced pressure if high purity is desired.

The following examples are offered by way of illustration and not by way of limitation.

EXAMPLE I

Preparation of 2-chloro-5,5-dimethyl-1,3,2-dioxaphosphorinane:

To phosphorus trichloride (775.4 g, 5.5 M, 10% molar excess) was added dropwise with stirring over two hours a solution of neopentylene glycol (520.8 g, 5.0 M) in chloroform (1200 ml). After the slight endotherm and evolution of HCl had subsided, the clear colorless solution was freed of most of the chloroform and excess $PCl_3$ by distillation at atmospheric pressure to a pot temperature of 100° C. Distillation of the residue through a short vacuum-jacketed Vigreaux column yielded 803.6 g (95.3% yield) of 2-chloro-5,5-dimethyl-1,3,2-dioxaphosphorinane (III), bp 65° C./10 mm $n_D^{25}$ 1.4738, % Cl found 20.71 (21.03 calculated).

EXAMPLE II

Preparation of intermediate 2-benzyloxy-5,5-dimethyl-1,3,2-dioxaphosphorinane (Formula II in which $R = R' =$ methyl and $Ar =$ phenyl):

To a stirred, cooled solution of benzyl alcohol (216.28 g, 2 moles) and triethylamine (222.2 g, 2.2 M) in toluene (600 ml) was added dropwise 2-chloro-5,5-dimethyl-1,3,2-dioxaphosphorinane (337.13 g, 2.0 M) from Example I. There was a vigorously exothermic reaction and a white precipitate was formed. After heating under reflux for 0.75 hr, the mixture was cooled, poured into water and shaken. The organic layer, after additional washing with water and $NaHCO_3$ solution, yielded, after stripping and fractional distillation, 415.1 g of colorless liquid bp 112° C. at 0.35 mm, $n_D^{25}$ 1.5111 and a further 28.4 g of a somewhat less pure forerun. Total yield = 443.5 g = 92.3%. ;p These results show that the desired novel compound was successfully produced in excellent yield and purity.

EXAMPLE III

Preparation of 2-benzyl-5,5-dimethyl-1,3,2-dioxaphosphorinane-2-one (Formula I in which $R = R' =$ methyl and $Ar =$ phenyl):

A mixture of 2-benzyloxy-5,5-dimethyl-1,3,2-dioxaphosphorinane (100 g, 0.416 M) from Example II, benzyl iodide (1.0 g), and xylene (50 ml) was heated until the temperature reached 165° C., and then slowly dropped to 155° C. After 1.5 hrs, the mixture was allowed to cool to yield 92.4 g (92.4% yield) of pure crystalline 2-benzyl-5,5-dimethyl-1,3,2-dioxaphosphorinane-2-one, melting point 109.5°–110.5° C. Analysis by gas-liquid chromatography showed no impurities present.

The mother liquid by GLC still contained all the benzyl iodide as well as traces of the product and the starting material. These results show that the desired compound was successfully produced by the process of this invention in excellent yield and purity.

EXAMPLE IV

Simplified preparation of the intermediate 2-benzyloxy-5,5-dimethyl-1,3,2-dioxaphosphorinane (Formula II wherein $R = R' = CH_3$ and $Ar =$ phenyl):

a. To a cooled solution of phosphorus trichloride (137.3 g, 1.0 M) in toluene (100 ml) was added dropwise with stirring below 30° C. a warm (60° C.) solution of neopentylene glycol (2,2-dimethyl-1,3-propanediol, 104.1 g, 10.M) in toluene (250 ml), followed by $2 \times 50$ ml hot toluene rinses of the addition funnel. After heating under reflux for 0.25 hr, the resulting clear, colorless solution was analyzed by GLC and found to contain 97.9% of the desired chloride.

b. The entire solution from (a) was added dropwise with stirring below 50° C. to a solution of benzyl alcohol (97.3 g, 0.9 M) and triethylamine (111.1 g, 1.1 M) in toluene (200 ml). After the addition, the mixture was heated under reflux for 0.75 hr and worked up as in Example II, omitting the distillation step, to yield 215.8 g of product which, by GLC, was 95.7% pure.

(Yield for Steps a+b combined: 89.8% based on neopentylene glycol (2,2-dimethyl-1,3-propanediol) + $PCl_3$ and 99.8% based on benzyl alcohol).

The results show that the desired novel compound was produced in high yield and purity.

EXAMPLE V

Conversion of Example IV intermediate to 2-benzyl-5,5-dimethyl-1,3,2-dioxaphosphorinan-2-one (Formula II wherein $R = R' =$ methyl and $Ar =$ phenyl):

203.0 g of the material prepared as above in Example IV was dissolved in xylene (100 ml) and heated to reflux. $3 \times 1.0$ g portions of benzyl iodide were added at 0, 2 and 4 hrs. After heating under reflux for 18 hrs. the mixture was diluted with 200 ml xylene and allowed to cool to yield 165.3 g (81.4% yield) of pure 1, mp 109.5°–110.5° C., 100% pure by GLC.

(Total overall yield based on neopentylene glycol + $PCl_3 =$ 73.3% based on benzyl alcohol = 81.2%).

The embodiments of the invention in which an exclusive property and privilege is claimed are defined as follows:

1. A process for preparing a 2-aralkyl-5,5-dialkyl-1,3,2-dioxaphosphorinan-2-one having the formula:

$$\begin{array}{c} R \\ \diagdown \\ C \\ \diagup \\ R' \end{array} \begin{array}{c} CH_2-O \\ \diagdown \\ \diagup \\ CH_2-O \end{array} \begin{array}{c} O \\ \diagup \\ P \\ \diagdown \\ CH_2Ar \end{array}$$

in which R is an alkyl group having 1 to 2 carbon atoms and R' is an alkyl group having 1 to 9 carbon atoms, and Ar is an aryl group having 6 to 18 carbon atoms, that comprises heating a 2-aralkyloxy-5,5-dialkyl-1,3,2-dioxaphosphorinane with a catalytic quantity of an aralkyl halide the halide being selected from the group consisting of bromine, chlorine and iodine, and recovering a 2-aralkyl-5,5-dialkyl-1,3,3-dioxaphosphorinan-2-one from the mixture.

2. A process according to claim 1 in which R and R' are methyl and Ar is phenyl.

3. A process according to claim 1 in which the aralkyl halide is an iodide.

4. A process according to claim 3, in which the iodide is benzyl iodide.

5. A process according to claim 1 in which the reaction mixture is heated at a temperature in the range from about 120° C. to 280° C.